US012274470B2

(12) United States Patent
Willard et al.

(10) Patent No.: US 12,274,470 B2
(45) Date of Patent: Apr. 15, 2025

(54) REMOVABLE, ADJUSTABLE-LENGTH, SNAP-IN PORTAL SAVER, DECOUPLED FROM DERMAL FIXATION

(71) Applicant: Conmed Corporation, Largo, FL (US)

(72) Inventors: Benjamin Willard, Clearwater, FL (US); Eric Subkjaer, Gulfport, FL (US)

(73) Assignee: Conmed Corporation, Largo, FL (US)

( * ) Notice: Subject to any disclaimer, the term of this patent is extended or adjusted under 35 U.S.C. 154(b) by 889 days.

(21) Appl. No.: 17/278,061

(22) PCT Filed: Oct. 3, 2019

(86) PCT No.: PCT/US2019/054520
§ 371 (c)(1),
(2) Date: Mar. 19, 2021

(87) PCT Pub. No.: WO2020/072786
PCT Pub. Date: Apr. 9, 2020

(65) Prior Publication Data
US 2021/0369302 A1 Dec. 2, 2021

Related U.S. Application Data

(60) Provisional application No. 62/741,806, filed on Oct. 5, 2018, provisional application No. 62/740,992, filed on Oct. 4, 2018.

(51) Int. Cl.
*A61B 17/34* (2006.01)
*A61B 17/00* (2006.01)

(52) U.S. Cl.
CPC .............. *A61B 17/3423* (2013.01); *A61B 2017/00367* (2013.01); *A61B 2017/00955* (2013.01);
(Continued)

(58) Field of Classification Search
CPC ...... A61B 17/3423; A61B 2017/00367; A61B 2017/00955; A61B 2017/00991;
(Continued)

(56) References Cited

U.S. PATENT DOCUMENTS 4,795,426 A * 1/1989 Jones ................ A61B 17/3421
604/164.11
5,657,963 A * 8/1997 Hinchliffe ............ A61M 39/06
604/167.01
(Continued)

FOREIGN PATENT DOCUMENTS

| EP | 2168510 | 3/2010 |
| WO | 2019118703 A1 | 6/2019 |

OTHER PUBLICATIONS

International Search Report Form PCT/ISA/220, International Application No. PCT/US2019/054520, pp. 1-15, Dated Aug. 31, 2020.
(Continued)

*Primary Examiner* — Tan-Uyen T Ho
*Assistant Examiner* — David P Stein
(74) *Attorney, Agent, or Firm* — Bond, Schoeneck & King, PLLC; Frederick J. M. Price

(57) ABSTRACT

A portal saver assembly with a dermal fixation device that is removably attached to a length-adjustable portal saver. The portal saver assembly includes a tubular body having a rigid proximal end with threads and a proximal adjustment body having an outer ridge and an inner bore with threads. The threads on the rigid proximal end of the tubular body are configured to mate with the threads on the inner bore of the proximal adjustment body. The portal saver assembly also includes a dermal fixation device with a central bore and a locking mechanism around the central bore. The outer ridge of the proximal adjustment body is removably attached to within the central bore by the locking mechanism.

23 Claims, 11 Drawing Sheets

(52) U.S. Cl.
CPC .............. *A61B 2017/00991* (2013.01); *A61B 2017/3443* (2013.01); *A61B 2017/3492* (2013.01)

(58) Field of Classification Search
CPC .... A61B 2017/3443; A61B 2017/3492; A61B 2017/3441; A61B 17/3462; A61B 2017/3488; A61B 17/3421; A61B 2017/3484; A61B 17/00234; A61B 90/08; A61B 2017/00238; A61B 2017/0034; A61B 2090/08021; A61B 17/3472; A61B 2017/347
See application file for complete search history.

(56) References Cited

U.S. PATENT DOCUMENTS

| | | | |
|---|---|---|---|
| 5,752,970 A | 5/1998 | Yoon | |
| 5,797,888 A | 8/1998 | Yoon | |
| 10,245,070 B2 | 4/2019 | Flom et al. | |
| 10,758,269 B2 * | 9/2020 | Morgan | A61B 17/3421 |
| 2003/0045834 A1 * | 3/2003 | Wing | A61B 17/3496 |
| | | | 604/161 |
| 2009/0306586 A1 * | 12/2009 | Ross | A61B 17/3439 |
| | | | 604/93.01 |
| 2010/0010449 A1 | 1/2010 | Leibowitz et al. | |
| 2010/0081871 A1 * | 4/2010 | Widenhouse | A61B 17/3462 |
| | | | 600/104 |
| 2010/0268241 A1 | 10/2010 | Flom et al. | |
| 2011/0144449 A1 | 6/2011 | Ortiz et al. | |
| 2012/0010563 A1 | 1/2012 | Ravikumar | |
| 2016/0100858 A1 * | 4/2016 | Flom | A61B 17/3421 |
| | | | 600/204 |
| 2017/0245888 A1 | 8/2017 | Buyda et al. | |

OTHER PUBLICATIONS

JP Office Action, App. No. 2021-518091, dated Jul. 5, 2022, pates 1-13.
"European Search Report, Application No. 23186926.4, dated Oct. 16, 2-23, pp. 1-9".
"CN Office Action, Application No. 201980065585.6, dated May 31, 2024, entire document".

* cited by examiner

REMOVABLE, ADJUSTABLE-LENGTH, SNAP-IN PORTAL SAVER, DECOUPLED FROM DERMAL FIXATION

CROSS-REFERENCES TO RELATED APPLICATIONS

This application is a national stage application under 35 U.S.C. 371 based on international patent application PCT/US19/54520 filed on Oct. 3, 2019, which claims priority to U.S. Provisional Patent Application Ser. No. 62/740,992 filed on Oct. 4, 2018, and entitled "Removable, Adjustable Length, Snap-in Portal Saver, Decoupled From Dermal Fixation," and U.S. Provisional Patent Application Ser. No. 62/741,806 filed on Oct. 5, 2018 and entitled "Removable, Ajusstable-Length Snap-in Portal Saver, Decoupled From Dermal Fixation," the entireties of which are incorporated herein by reference.

BACKGROUND OF THE INVENTION

1. Field of the Invention

The present invention is directed generally to a portal saver device and, more particularly, to a portal saver assembly with a dermal fixation device that is removably attached to a length-adjustable portal saver.

2. Description of Related Art

In order to maintain arthroscopic intra-articular hip joint access, a series of access tools (switching stick, slotted cannula, disposable cannula, etc.) are conventionally used frequently for insertion and removal of the instruments performing work on the patient. The use of access tools account for a great percentage of the time spent in procedure by the surgeon. During the time spent using the access tools, the surgeon is not performing any actual work on the patient's pathology.

A common access tool in the field of arthroscopic surgery is a "cannula." The cannula is used to maintain an open portal leading from outside the patient's body to inside the body to the location where the arthroscopic procedure is to be performed. It is important that this cannula stay inside the body, maintain this path, and not fall out, migrate outward, or migrate farther inward. This is accomplished by a number of means today, most frequently by placing aggressive threads on the outside of the cannula to auger (or drill) into the dermal layer and tissue below it. This can require a sizable incision be made to admit such screw threads, resulting in a corresponding-sized scar.

Current cannulas mostly use mechanical threads on the exterior of the tube-like body of the cannula itself. Some of these cannulas have stiff tube-like bodies or less rigid bodies with virtually no radial movement. While some current cannulas are more flexible, they are still not flexible enough to accommodate a wide range of instruments. Conventional cannulas additionally have a fluid seal on the proximal end to prevent the leakage of fluid from the surgical site. Some cannulas also include indicators along the tube-like body for customizing the size of the tube-like body. These cannulas are often screwed in with an obturator.

Some cannulas alternatively or additionally have barbs, and these cannulas can be inserted straight into the surgical site while benefiting from a bit of oscillating rotation during advancement into the body. Still, cannulas use a collapsing accordion-like member which can be stretched to decrease its diameter and compressed to increase its diameter. None of these conventional cannulas, however, provide the large displacement of rigid bodies sub-dermally that allow insertion and subsequent removal through a small incision. Further, none of these conventional cannulas provide for a small incision size or minimize trauma to the region surrounding the incision site. Even further, none of the conventional cannulas provide a wide a range of motion and freedom.

Achieving dermal fixation and inserting a means of dermal fixation during conventional cannula insertion can often be accompanied by large forceful motions and twisting motions while attempting to drive dermal fixation structures through and into the patient. If portal saver is attached to the dermal fixation while this is being done, there could be potential for the distal end of the portal saver itself to move about in ways that could pose a risk to structures deep inside the patient. Also, during surgery, it can be necessary to remove the portal saver, such as to trim it to a shorter working length. Or, it can be necessary to replace the portal saver with a longer portal saver.

Therefore, a need exists for a portal saver assembly with a dermal fixation device that is removably attached to a length-adjustable portal saver.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a portal saver assembly with a dermal fixation device that is removably attached to a length-adjustable portal saver. According to one aspect, the present invention is a portal saver device. The portal saver device includes a tubular body having a flattened section between two rounded sections and a rigid proximal end with threads. The device also includes a proximal adjustment body having an inner bore with threads. The threads on the rigid proximal end of the tubular body are configured to mate with the threads on the inner bore of the proximal adjustment body. In a first configuration, the flattened section is a first distance from proximal adjustment body. In a second configuration, the flattened section is a second distance from the proximal adjustment body, and the second distance is smaller than the first distance.

According to another aspect, the present invention is portal saver assembly. The portal saver assembly includes a tubular body having a rigid proximal end with threads and a proximal adjustment body having an outer ridge and an inner bore with threads. The threads on the rigid proximal end of the tubular body are configured to mate with the threads on the inner bore of the proximal adjustment body. The portal saver assembly also includes a dermal fixation device with a central bore and a locking mechanism around the central bore. The outer ridge of the proximal adjustment body is removably attached to within the central bore by the locking mechanism.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
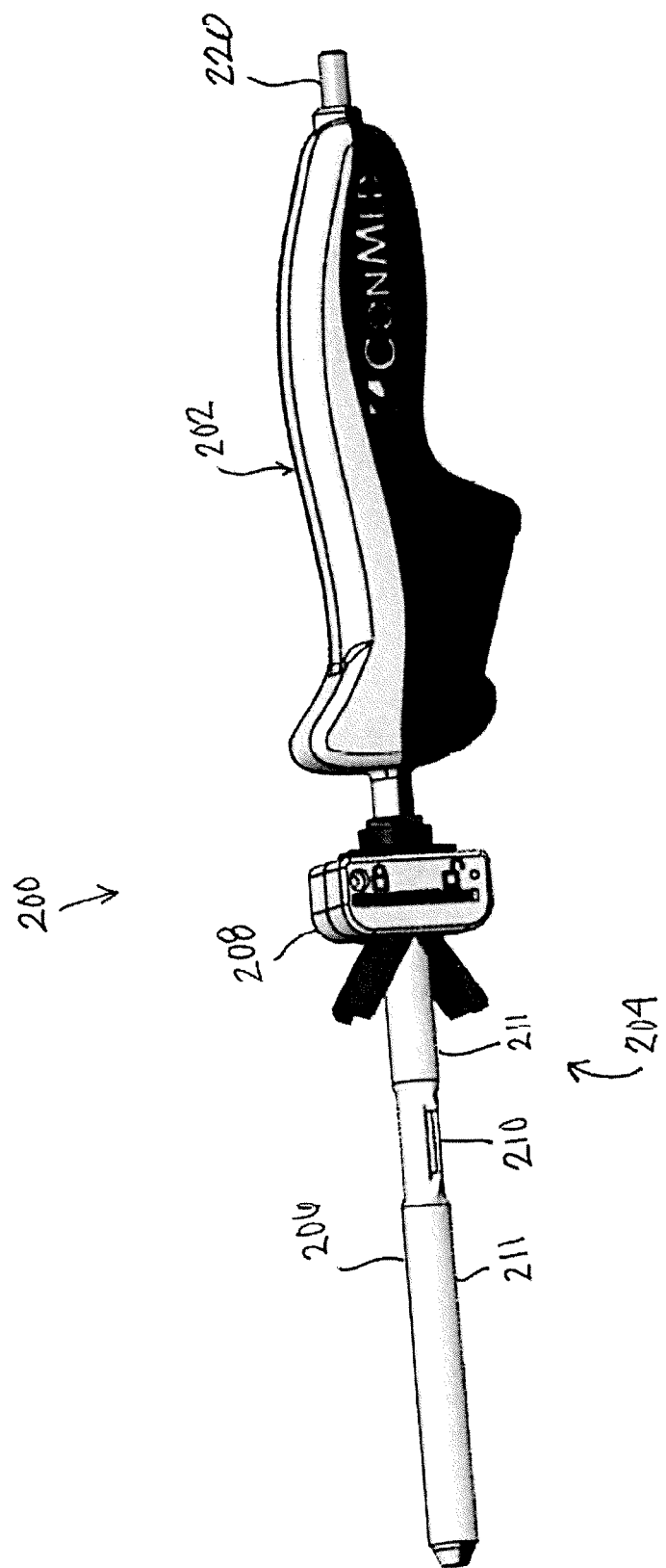
FIG. 1 is a perspective view of an exemplary portal saver assembly, according to an embodiment.

Referring now to the figures, wherein like reference numerals refer to like parts throughout, FIG. 1 shows a perspective view of an exemplary portal saver assembly 200. In general, a portal saver and obturator assembly 200 maintains the path from outside the body (e.g., the skin) to the surgical site (e.g., the joint), which allows the surgeon to move an instrument from one portal to another in two steps or actions (as opposed to 9 steps or actions with conventional devices). A portal saver and obturator assembly 200 typically includes a proximal handpiece 202 configured to removably attach to a portal saver assembly 204. The portal saver assembly 204 comprises a distal tubular (or cannulated) body 206 extending from a proximal dermal fixation device 208. A purpose of an embodiment of the present invention is to allow for the proximal dermal fixation device 208 shown in FIG. 1 to decouple from the tubular body 206, while providing a mechanism for adjusting the length of the tubular body 206.

The tubular body 206 is preferably flexible. It can be composed of thermoplastic urethane (hereinafter "TPU")). TPU is a thermoplastic elastomer comprising block copolymers. Specifically, TPU comprises linear alternating hard segments and soft segments—as should be understood by those of ordinary skill in the art. The hard segments are composed of diisocyanates with short-chain diols (i.e., "chain extenders"), making them short, high polarity segments. The soft segments are composed of diisocyanates with long-chain diols, making them long, low polarity segments.

The rigidity of TPU can be fine-tuned by increasing or decreasing the ratio of hard segments to soft segments. TPU has high mechanical properties, high heat resistance, high resistance to mineral oils, high hydrolysis resistance, high low-temperature flexibility, high resistance to microbiological degradation, and high elasticity across the entire hardness range. TPU has a hardness of 30 Shore A to 60 Shore D under standard atmospheric conditions—as should be understood by those of ordinary skill in the art in conjunction with a review of this disclosure. An example of TPU is Elastollan®. Another example of TPU is Isothane grade 5090A, made by Greco.

TPU provides a number of advantages for use as the composition for the tubular body 206. In an embodiment, the tubular body 206 is formed via extrusion and is an extruded TPU composition that can retain its shape after being manipulated. It is more flexible and thinner than conventional cannulas and can be moved into various twisted and knotted configurations. The flexibility and resiliency of the tubular body 206 gives a better range of motion for the surgeon, as if they were operating percutaneously. The tubular body 206 is free to move anywhere and is only limited during use by the proximal dermal fixation device 208, which is fixed to the dermis. TPU is also resistant to cuts or other damage from sharp instruments, such as a shaver blade or bur. Further, the heat resistant qualities TPU mentioned briefly above allow for the passage of ablation instruments without deformation or other damage to the tubular body 206.

In alternative embodiments, there are one or more seals along a length of the tubular body 206. The seals can be angled or perpendicular to each other along the longitudinal axis of the tubular body 206 (which is approximately parallel to the length to the tubular body 206). In other embodiments, the tubular body 206 comprises indicators along its length for customizing the size of the obturator 204.

Figure 2:
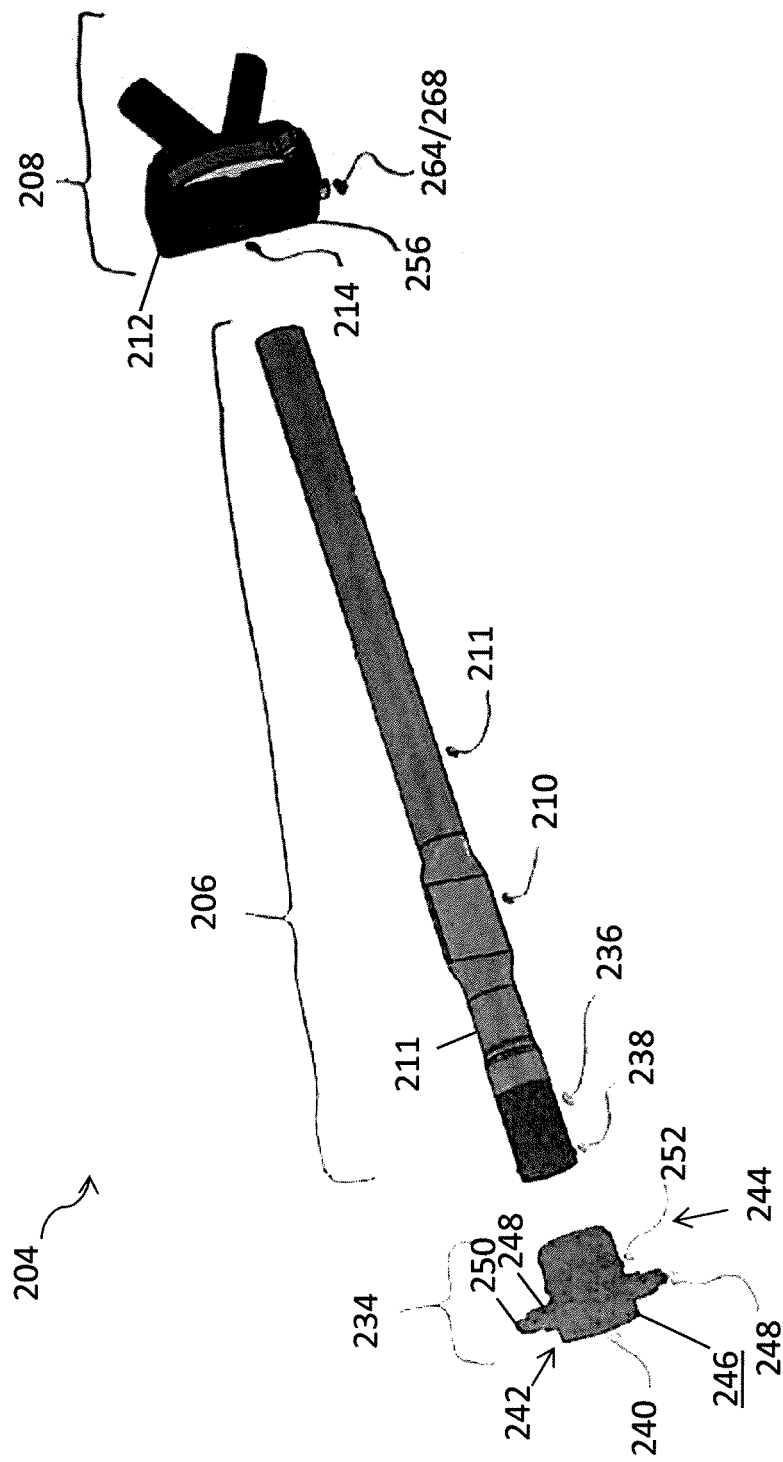
FIG. 2 is an exploded perspective view schematic representation of a portal saver assembly, according to an embodiment.

Turning now to FIG. 2, there is shown an exploded perspective view schematic representation of an obturator 204 of a portal saver assembly 200, according to an embodiment. As shown, the tubular body 206 of the portal saver assembly 204 has two round sections 211 with the flattened section 210 therebetween. The flattened (or narrow) section 210 acts as a seal and can be constructed through heat forming processes. The flattened section 210 is heat sealed to make the tubular body 206 flat. The flattened section 210 can be used as an alternative to a welded flat sheet material with seams. In some situations, the flattened section 210 for the tubular body 206 is preferable to welded seams because the compression force on the tubular body 206 with welded seams creates high frictions, which tends to grab onto instruments within the tubular body 206. This can lead to accidental withdraw of instruments from a portal and can add a dimension (i.e., "noise) to the sense of feel for the surgeon. The flattened section 210 forms a seal between itself and an instrument extending through the tubular body 206. Thus, the tubular body 206 is tighter around the instrument. After the instrument is removed, the flattened section 210 (i.e., the heat pressed or sealed portion) returns to the flat shape. The flattened section 210 also prevents fluid from leaking out of the tubular body 206 from the incision site. The flat region 210 can be located anywhere along the tubular body 206. The flat region 210 can be located directly between the proximal end and the distal end of tubular body 206, closer to the proximal end of the tubular body 206, or closer to the distal end of the tubular body 206. For example, in the circumstance where the flat region 210 is located closer to the proximal end of the tubular body 206, there is more tubular body 206 positioned distally to the flat region 210 in order to increase the range of sizes a surgeon can trim to for maximum length adjustability.

Still referring to FIG. 2, the tubular body 206 extends distally from an adjustment body 234 and the adjustment body 234 is configured to releasably connect to the proximal dermal fixation device 208. The tubular body 206 includes a rigid proximal end 236. The rigid proximal end 236 is a non-flexible lead-in portion of the tubular body 206. The rigid proximal end 236 functions to provide a secure, stable connection between the tubular body 206 and the adjustment body 234. The rigid proximal end 236 comprises threads 238 for attachment to the adjustment body 234. The threaded, rigid distal end 244 also serves as a length adjusting mechanism for telescoping the tubular body 206, as described in detail below.

As shown in FIG. 2, the adjustment body 234 comprises a threaded inner bore 240. The threaded inner bore 240 extends entirely through the adjustment body 234 from its proximal end 242 to its distal end 244. The adjustment body 234 also comprises an outer surface 246 having an adjustment wheel 248 extending radially therefrom. The adjustment wheel 248 extends around the entire circumference of the adjustment body 234. The adjustment wheel 248 may have protrusions 250 (or other like projections/ridges) extending radially therefrom to improve the grip of the user and can be used during procedures for length adjustment. The adjustment body 234 additionally includes a ridge 252 extending around its entire circumference, as shown in FIG. 2. The ridge 252 extends radially from the adjustment body 234. In the depicted embodiment, the ridge 252 is distal relative to the adjustment wheel 248.

Figure 3:
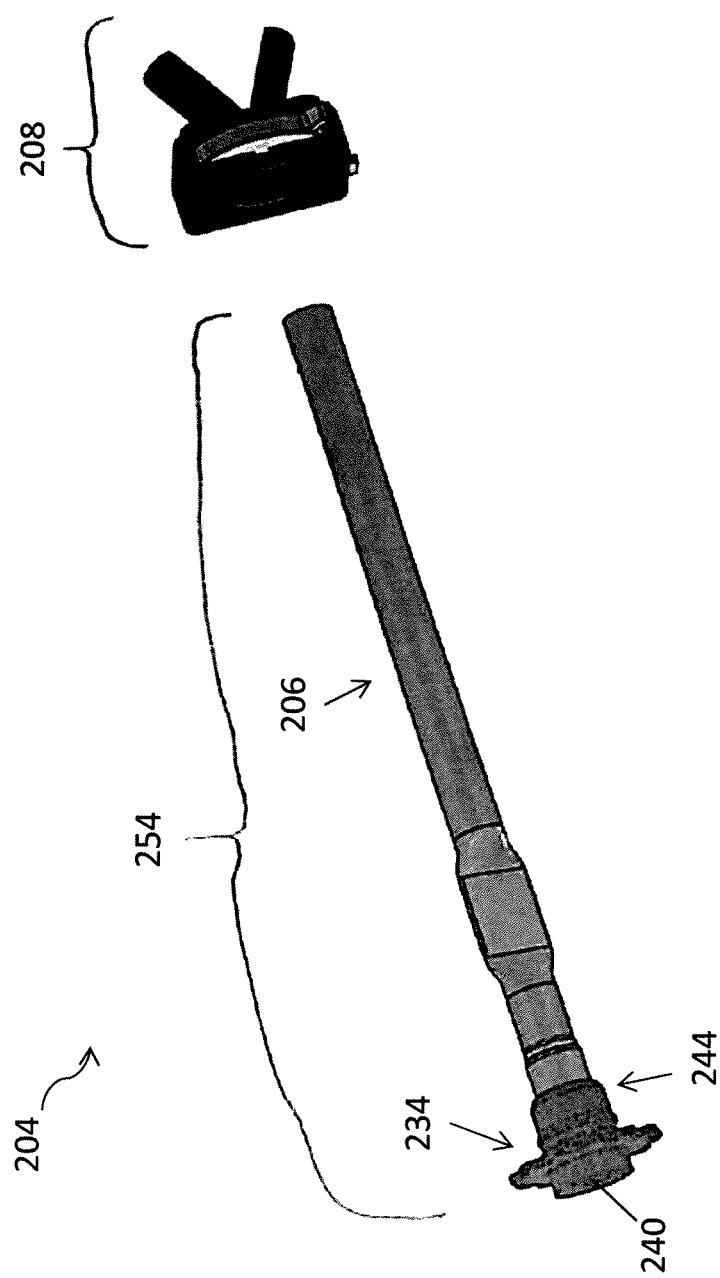
FIG. 3 is a partial exploded perspective view schematic representation of a portal saver assembly, according to an embodiment.

Turning now to FIG. 3, there is shown a partial exploded perspective view schematic representation of the portal saver assembly 204 of a portal saver and obturator assembly 200, according to an embodiment. As shown in FIG. 3, the adjustment body 234 is connected to the tubular body 206. The rigid proximal end 236 and threads 238 (FIG. 2) of the tubular body 206 are threaded into the threaded inner bore 240 from the distal end 244 of the adjustment body 234, resulting in an adjustable-length portal saver device 254. As mentioned above, the portal saver device 254 can be removably connected to the dermal fixation device 208.

Referring briefly back to FIG. 2, the proximal end 242 of the adjustment body 234 can be removably attached to the dermal fixation device 208. The dermal fixation device 208 comprises a body 212 (e.g., rectangular body) with a central bore 214 extending therethrough. As shown in the exemplary embodiment of FIG. 4, the central bore 214 extends through a rotating portion 216 and a non-rotating portion 218. The rotating portion 216 and the non-rotating portion 218 are configured to work in conjunction to fine tune the attachment of the dermal fixation device 208 to a tube-like (or cannulated) rod 220 of the handpiece 202, as shown in FIG. 1. A handpiece 202 may be temporarily connected to the dermal fixation device 208 in order to insert and deploy the dermal fixation device 208 (separate from the portal saver device 254).

The rotating portion 216 is a movable female connector, such as a threaded channel 222 extending from the central aperture 214. The non-rotating portion 218 is a non-threaded (or relatively smooth) channel 224 connected within the threaded channel 222. The non-threaded channel 222 is also connected to the tubular body 206 near the flattened section 210, as shown. When the dermal fixation device 208 is attached to the handpiece 202, the rotating portion 216 and the non-rotating portion 218 receive the tube-like rod 220 and the rotating portion 216 is rotated such that the threaded channel 222 tightens around the tube-like rod 220. In use, instruments can be inserted proximally into the tube-like rod 220 and pass through the tubular body 206.

Figure 4:
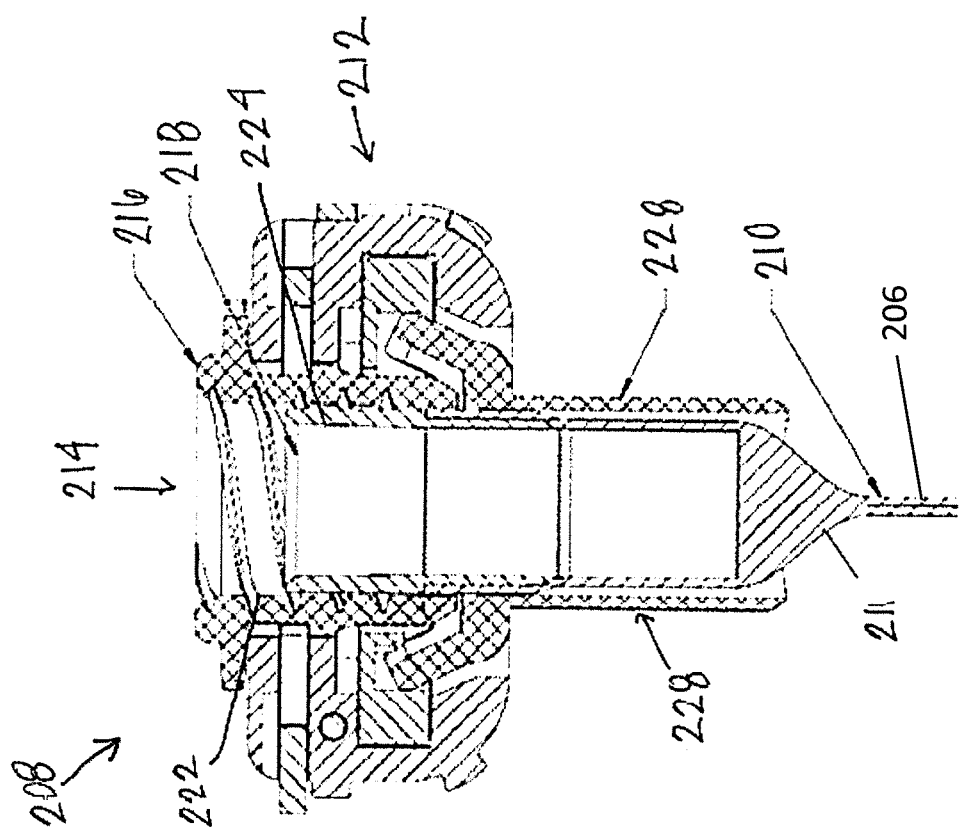
FIG. 4 is a detailed side section view schematic representation of the proximal dermal fixation device of the portal saver assembly, according to an embodiment.
Figure 5:
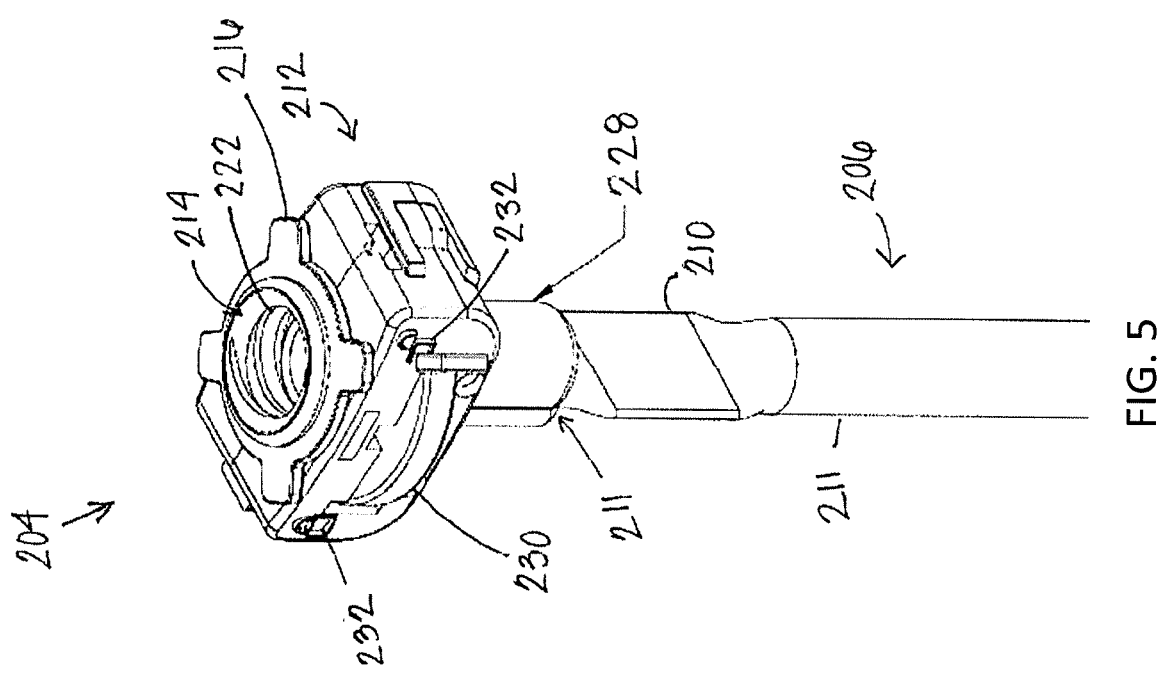
FIG. 5 is a top perspective view schematic representation of the portal saver assembly in a first configuration, according to an embodiment.

Turning now to FIG. 5, there is shown a top perspective view schematic representation of the obturator 204 in a first configuration, according to an embodiment. The dermal fixation device 208 comprises one or more petals 228 extending distally from within the body 212 of the dermal fixation device 208 (also shown in FIG. 4). The petals 228 are movable from a first configuration to a second configuration using an actuator 230 on the body 212. As shown in FIGS. 4 and 5, the petals 228 are in the first configuration, closed against the tubular body 206. In the depicted embodiment, the petals 228 extend in a direction parallel to a length of the tubular body 206 in the first configuration. When the petals 228 are in the first configuration, the actuator 230 is in a first position, as shown. In an embodiment, the first position is the unlocked position wherein the petals 228 are approximately flush with the tubular body 206 for insertion into the patient.

Figure 6:
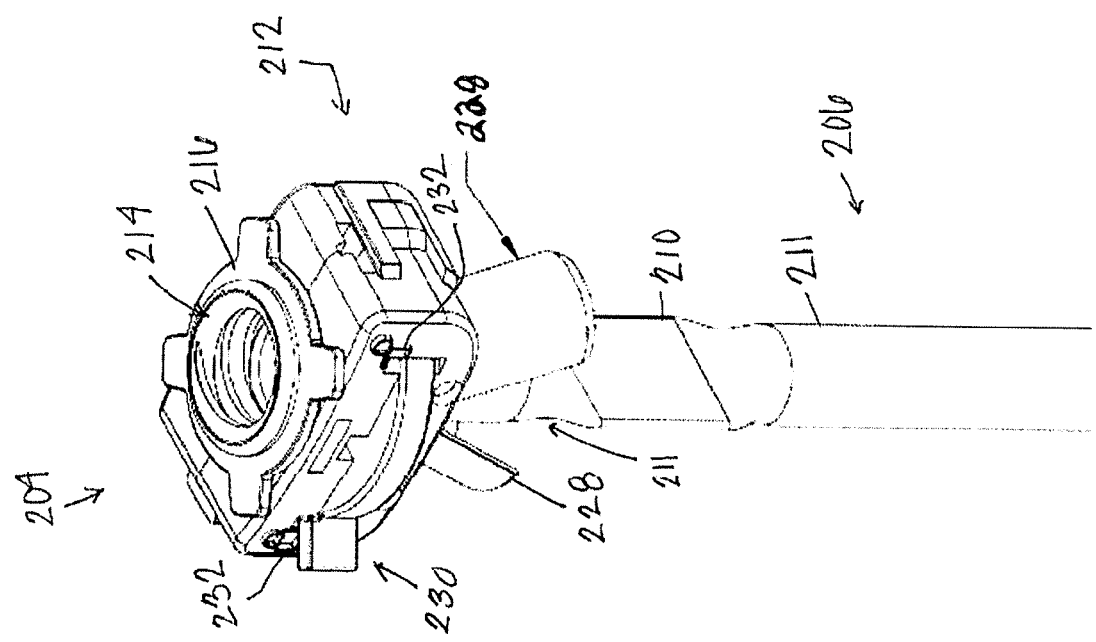
FIG. 6 is a top perspective view schematic representation of the portal saver assembly in a second configuration, according to an embodiment.
Figure 7:
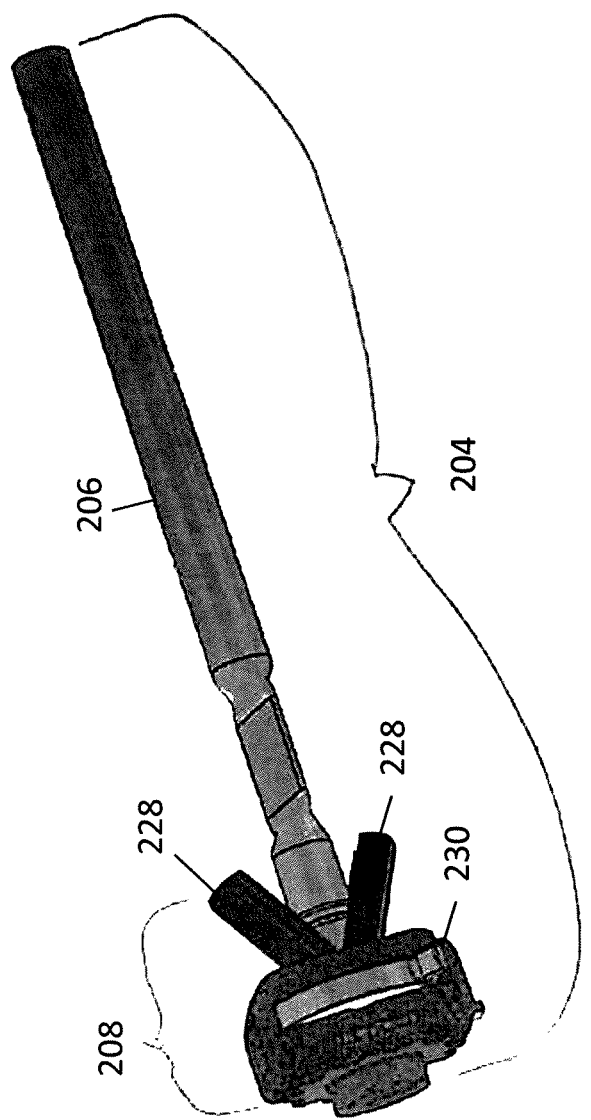
FIG. 7 is a perspective view schematic representation of the portal saver assembly in a second configuration, according to an embodiment.
Figure 8:
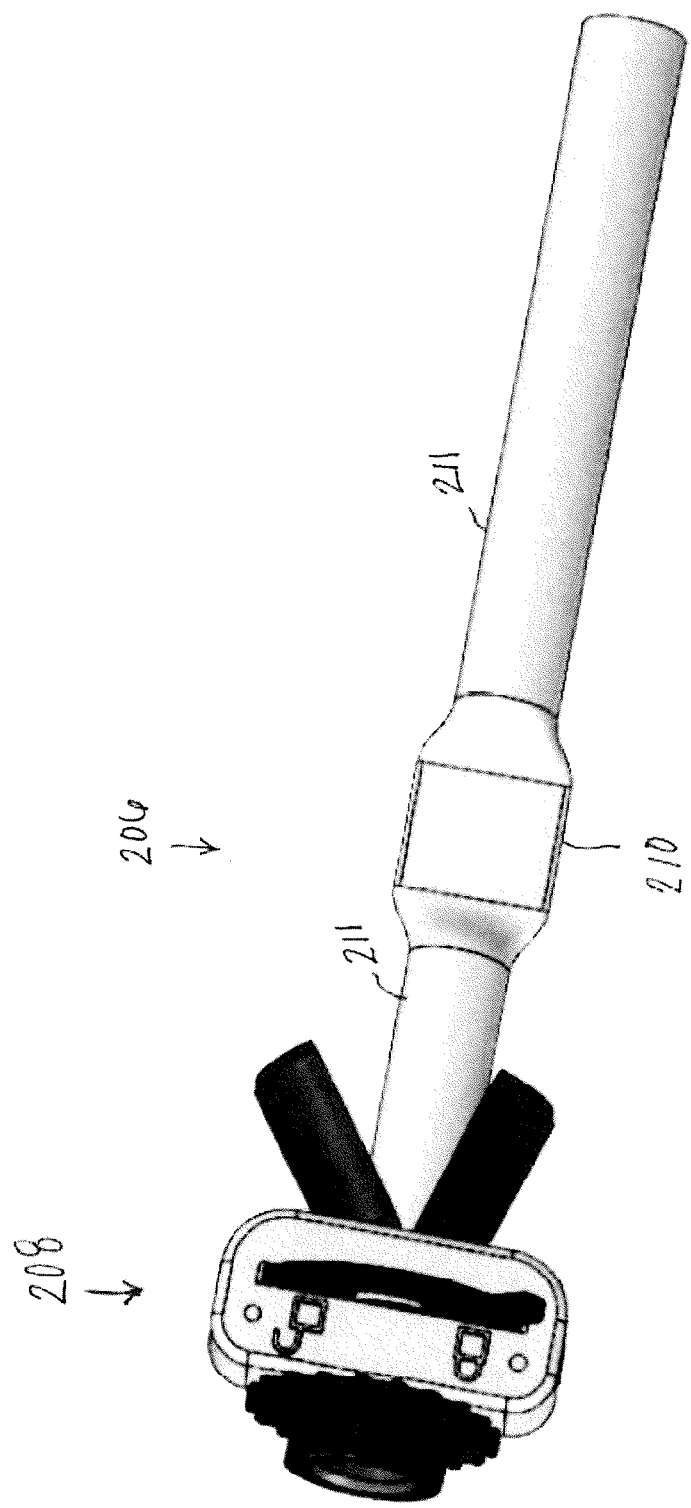
FIG. 8 is another perspective view schematic representation of the portal saver assembly in a second configuration, according to an embodiment.

Turning now to FIGS. 6-8, the petals 228 are in the second configuration. To move the petals 228 into the second configuration, the actuator 230 is activated. In the depicted embodiment, the actuator 230 is rotated or otherwise moved to a second position. (The first and second positions of the actuator 230 can be denoted by indicators 232 on the 212, as shown in FIG. 6). When the petals 228 are in the second configuration, they are expanded and extending at an angle relative to the tubular body 206, as shown. In the second configuration, the petals 228 function to retain the portal saver assembly 204 within the patient.

Figure 9:
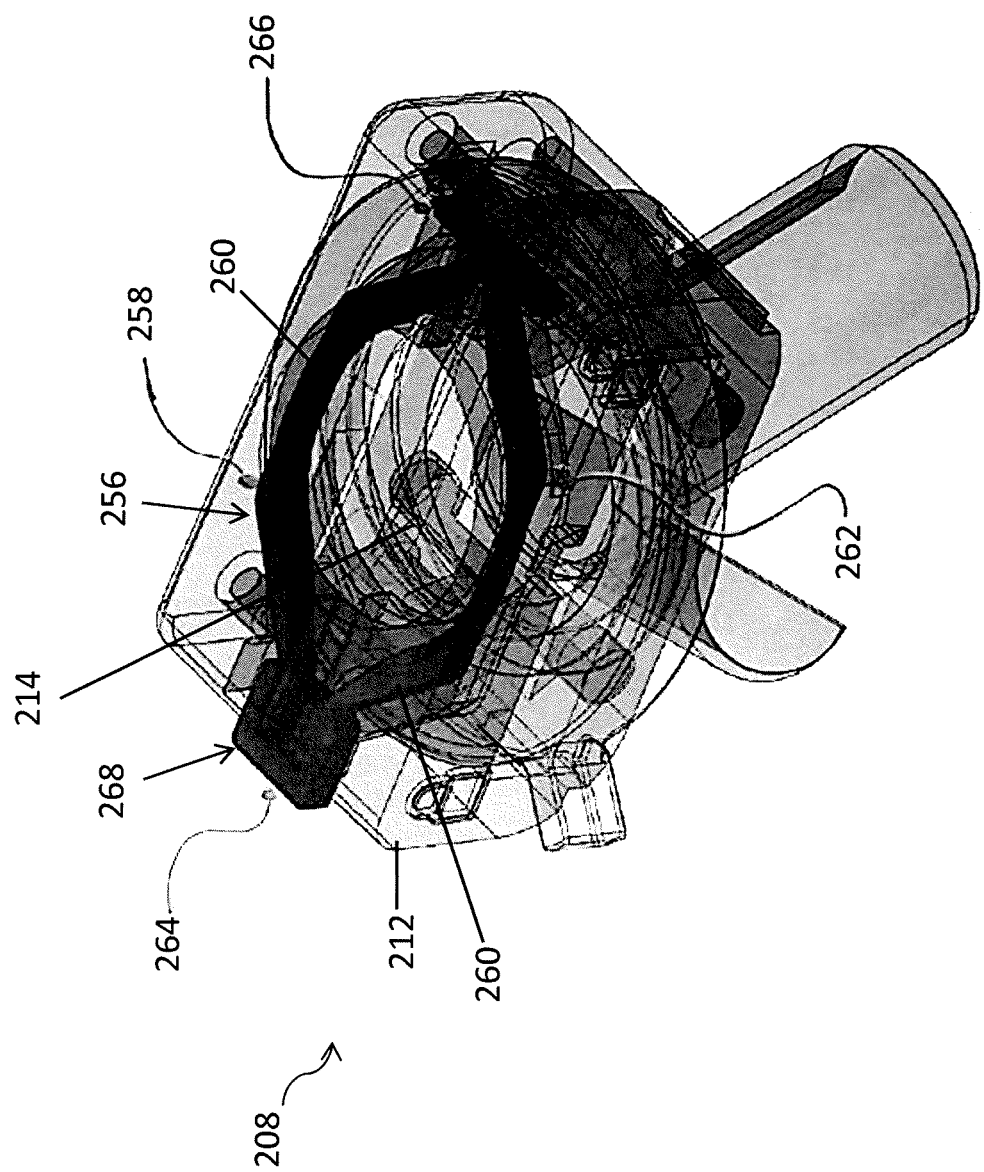
FIG. 9 is a top perspective view schematic representation of the proximal dermal fixation device of the portal saver assembly, according to an embodiment.

Referring now to FIG. 9, there is shown a top perspective view schematic representation of the proximal dermal fixation device 208 of the portal saver assembly 204, according to an embodiment. The proximal dermal fixation device 208 of FIGS. 2 and 11 comprises a central bore 214 extending therethrough. The central bore 214 is configured to receive the ridge 252 of the adjustment body 234 (FIG. 2). In an embodiment, the ridge 252 of the adjustment body 234 is configured to snap into the central bore 214.

Figure 11:
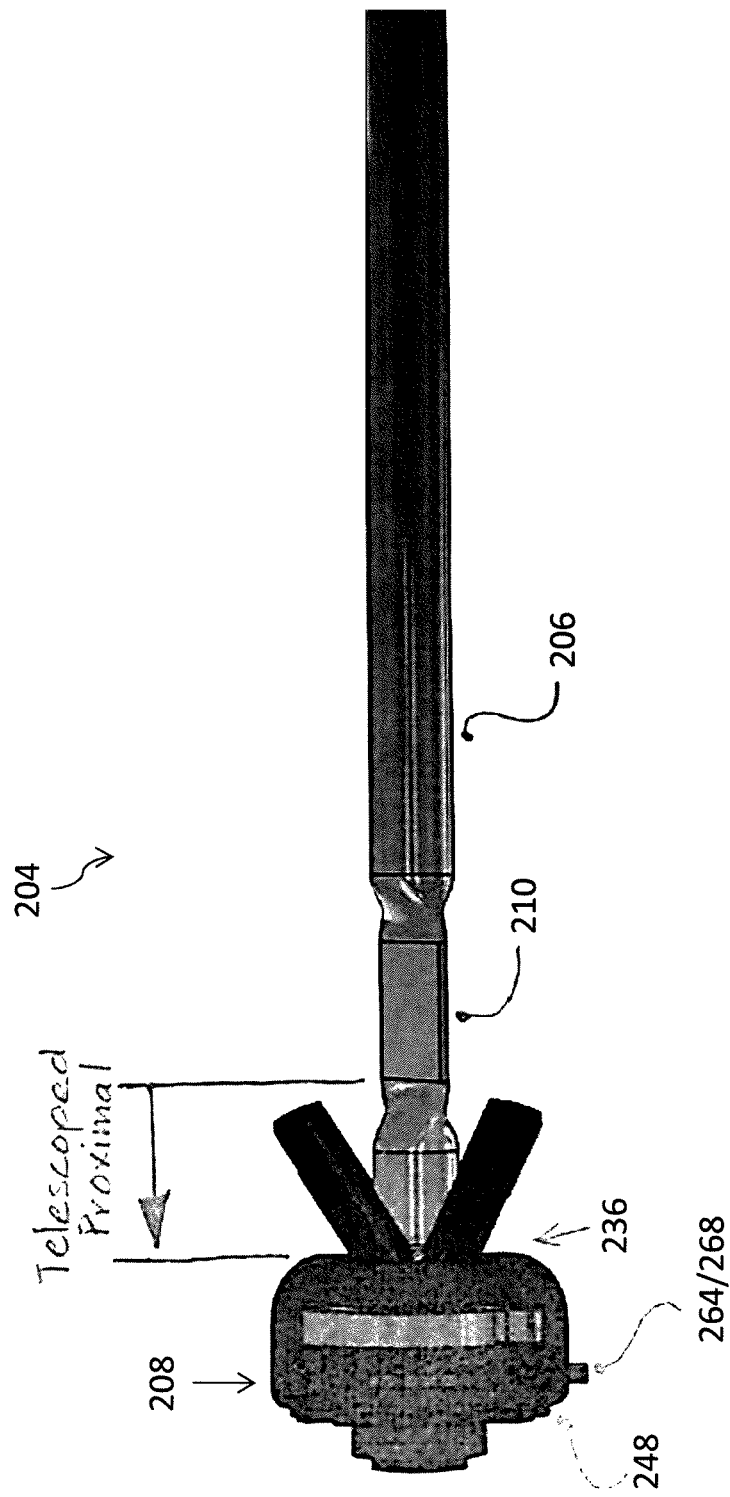
FIG. 11 is a side view schematic representation of the portal saver assembly in a retracted position, according to an embodiment.

The dermal fixation device 208 of FIGS. 2 and 11 also comprises a locking mechanism 256. In the depicted embodiment, the locking mechanism 256 is a spring clip. In the depicted embodiment, the spring clip 256 is a double-wishbone shaped retaining spring clip. In other words, it comprises a bowed first arm 258 with three connected, substantially straight segments 260 and a bowed second arm 262 with three connected, substantially straight segments 260. The first arm 258 and the second arm 262 are oriented or otherwise arranged such that they unite or meet within the body 212 of the dermal fixation device 208, forming a substantially hexagonal shape. The spring clip 256 is configured to snap over the ridge 252 of the adjustment body 234.

The spring clip 256 comprises an exposed portion 264 and a non-exposed portion 266. As shown in FIG. 11, the non-exposed portion 266 is within the body 212 of the dermal fixation device 208. The non-exposed portion 266 includes the first arm 258 and the second arm 262 of the spring clip 256. The exposed portion 264 is a tab 268 attached to both the first arm 258 and the second arm 262. The tab 268 extends from the body 212 of the dermal fixation device 208, as shown in FIGS. 2 and 11. By depressing the tab 268 toward the body 212 of the dermal fixation device 208, the spring clip 256 is opened. In other words, by pushing the tab 268 inward, the first arm 258 and the second arm 262 move away from each other in opposing directions, opening the spring clip 256.

When the spring clip 256 is opened (by pressing the tab 268), the ridge 252 of the adjustment body 234 can be inserted therein. Then, when the tab 268 is released, it catches or otherwise snaps onto the ridge 252 of the adjustment body 234, locking the tubular body 206 into the dermal fixation device 208, as shown in FIG. 7. To release the ridge 252 of the adjustment body 234, the tab 268 is pressed again, thereby opening the spring clip 256 and releasing the adjustment body 234 (with the attached tubular body 206), as shown in FIG. 3. Thus, the adjustment body 234 can be coupled to and decoupled from the dermal fixation device 208. This allows for removal of the portal saver device 254, as shown in FIG. 3. In other words, the dermal fixation device 208 can be inserted and deployed before the portal saver device 254 (with its integrated length adjustment) is added. The decoupling also allows for potentially safer insertions of both the dermal fixation device 208 and the portal saver device 254.

Figure 10:
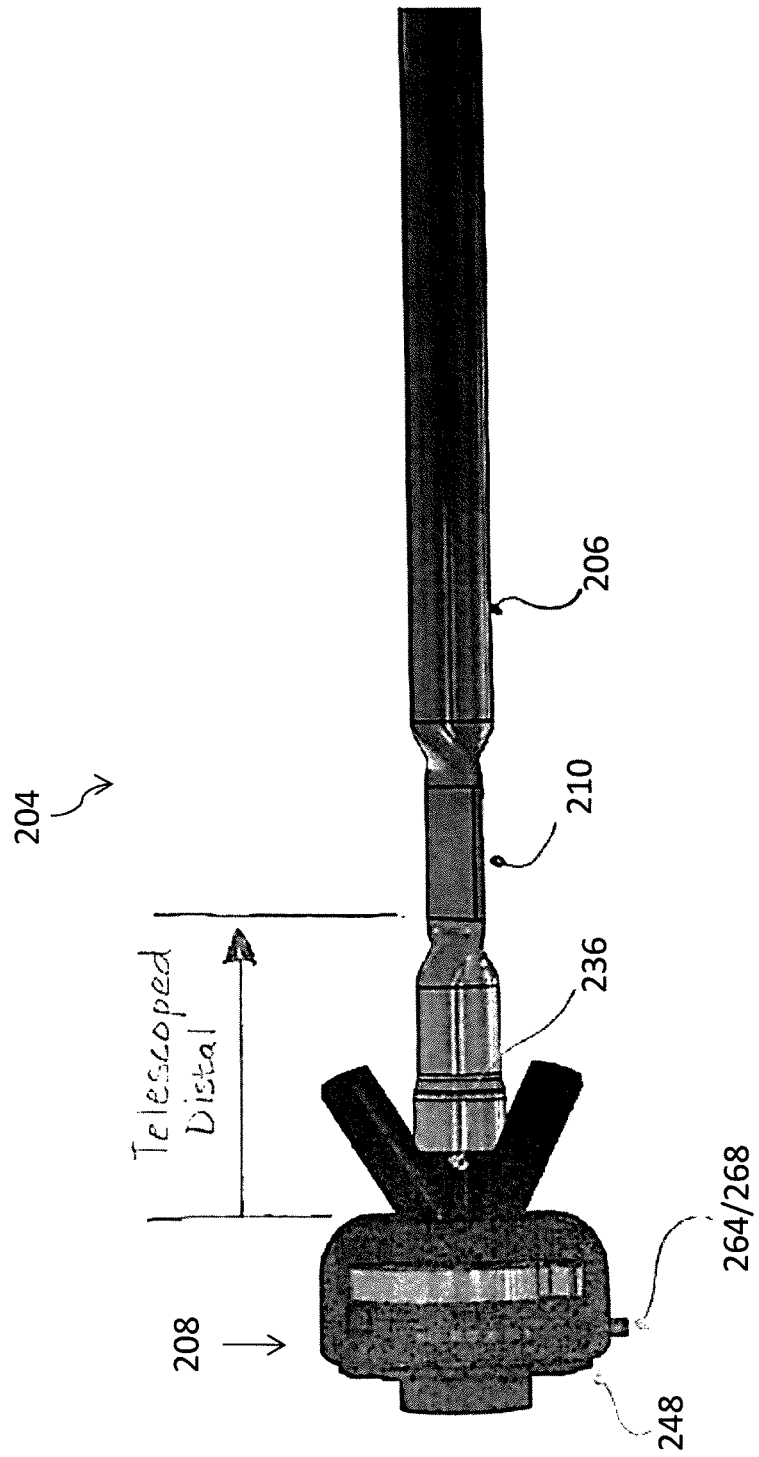
FIG. 10 is a side view schematic representation of the portal saver assembly in an extended position, according to an embodiment.

Referring now to FIG. 10, there is shown a side view schematic representation of the obturator 204 in an extended position, according to an embodiment. In the extended position, the flat section 210 of the tubular body 206 is a first distance from the dermal fixation device 208. To achieve the extended position, the adjustment wheel 248 is rotated in a first direction, exposing the rigid proximal end 236 and thereby causing the tubular body 206 to be telescoped in a distal direction. This increases the working length of the entire portal saver assembly 200. The adjustment wheel 248 can be rotated at any time during a procedure to lengthen the portal saver assembly 200.

Turning now to FIG. 11, there is shown a side view schematic representation of the portal saver assembly 204 in a retracted position, according to an embodiment. In the retracted position, the flat section of the tubular body 206 is a second distance from the dermal fixation device 208. In an embodiment, the second distance is shorter or smaller than the first distance. To achieve the retracted position, the adjustment wheel 248 is rotated in a second direction, opposing the first direction, which brings the rigid proximal end 236 into the dermal fixation device 208. Turning the adjustment wheel 248 in the second direction causes the tubular body 206 to be telescoped in a proximal direction. This decreases the working length of the entire portal saver assembly 204. The adjustment wheel 248 can be rotated at any time during a procedure to shorten the portal saver assembly 204.

In use, the dermal fixation device 208 is advanced (via the handpiece 202 in FIG. 1, for example) into the incision site without posing any risk to surrounding structures (e.g., femoral head) due to its small diameter. (The dermal fixation device 208 can be configured for the dermal openings used in most procedures, including a 12 mm dermal opening diameter, which is smaller than that used for most cannulas). The dermal fixation device 208 is advanced farther until the petals 228 are in the dermal layer. The actuator 230 is then moved from the first position to the second position, deploying the petals 228 and moving them from the first configuration to the second configuration.

With the dermal fixation device 208 in place, fixed to the dermal layer, the portal saver device 254 can be coupled to the dermal fixation device 208. The user presses the tab 268 inward, moving the first arm 258 and the second arm 262 away from each other in opposing directions and opening the spring clip 256. While pressing the tab 268 toward the body 212 of the dermal fixation device 208, the user inserts the ridge 252 of the adjustment body 234, which is configured to snap into the central bore 214. Then, the tab 268 is released and the spring clip 256 locks around and onto the adjustment body 234 (at the ridge 252), coupling the portal saver device 254 and the dermal fixation device 208. With the portal saver device 254 coupled to the dermal fixation device 208, the length of the portal saver device 254 can be adjusted during a procedure using the adjustment body 234, as described above. When use of the portal saver device 254 is complete, the user can press the tab 268 inward toward the body 212 of the dermal fixation device 208 again, releasing the ridge 252 from the spring clip 256. With the ridge 252 released, the user can remove the portal saver device 254 from the dermal fixation device 208 and from the original incision for easy removal without causing additional trauma or scarring to the skin or dermis of the patient.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A portal saver device, comprising:
    a tubular body having a flattened section between two rounded sections having a first proximal end and a second distal end, respectively, and a rigid proximal end with threads, wherein the flattened section is closer to the first proximal end than the second distal end;
    a proximal adjustment body having an inner bore with threads;
    wherein the threads on the rigid proximal end of the tubular body are configured to mate with the threads on the inner bore of the proximal adjustment body;
    wherein in a first configuration, the flattened section is a first distance from proximal adjustment body;
    wherein in a second configuration, the flattened section is a second distance from the proximal adjustment body.

2. The device of claim 1, further comprising an adjustment wheel extending radially from the proximal adjustment body.

3. The device of claim 2, wherein the adjustment wheel is rotatable in a first direction and an opposing, second direction.

4. The device of claim 3, wherein rotating the adjustment wheel in the first direction moves the flattened section away from the proximal adjustment body.

5. The device of claim 3, wherein rotating the adjustment wheel in the second direction moves the flattened section toward the proximal adjustment body.

6. The device of claim 1, wherein the second distance is different from the first distance.

7. The device of claim 6, wherein the second distance is shorter than the first distance.

8. A portal saver assembly, comprising:
    a tubular body having a flattened section between two rounded sections having a first proximal end and a second distal end, respectively, and a rigid proximal end with threads, wherein the flattened section is closer to the first proximal end than the second distal end;
    a proximal adjustment body having an outer ridge and an inner bore with threads;
    wherein the threads on the rigid proximal end of the tubular body are configured to mate with the threads on the inner bore of the proximal adjustment body;
    a dermal fixation device with a central bore and a locking mechanism around the central bore;
    wherein the outer ridge of the proximal adjustment body is removably attached within the central bore by the locking mechanism.

9. The assembly of claim 8, wherein the locking mechanism is a spring clip.

10. The assembly of claim 9, wherein the spring clip comprises a first arm and a second arm, which are movable toward and away from one another.

11. The assembly of claim 9, wherein the spring clip comprises an exposed portion outside the dermal fixation device and a non-exposed portion within the dermal fixation device.

12. The assembly of claim 11, wherein the exposed portion is moveable toward the dermal fixation device.

13. The assembly of claim 12, wherein pressing the exposed portion toward the dermal fixation device opens the spring clip.

14. The assembly of claim 8, wherein in a first configuration, the flattened section is a first distance from proximal adjustment body.

15. The assembly of claim 14, wherein in a second configuration, the flattened section is a second distance from the proximal adjustment body.

16. The assembly of claim 8, further comprising an adjustment wheel extending radially from the proximal adjustment body, wherein the adjustment wheel is rotatable in a first direction and an opposing, second direction.

17. The assembly of claim 16, wherein rotating the adjustment wheel in the first direction moves the flattened section away from the proximal adjustment body and rotating the adjustment wheel in the opposing, second direction moves the flattened section toward the proximal adjustment body.

18. The assembly of claim 8, further comprising one or more petals extending distally from the dermal fixation device.

19. The assembly of claim 18, wherein in a first configuration, the petals extend along the length of the tubular body.

20. The assembly of claim 18, wherein in a second configuration, the petals extend at an angle relative to the length of the tubular body.

21. The assembly of claim 8, wherein the tubular body is composed of thermoplastic urethane (TPU).

22. The device of claim 15, wherein the second distance is different from the first distance.

23. The device of claim 22, wherein the second distance is shorter than the first distance.

* * * * *